United States Patent [19]

Chang et al.

[11] Patent Number: 4,477,571
[45] Date of Patent: Oct. 16, 1984

[54] CHIMERIC PLASMIDS THAT REPLICATE IN BACTERIA AND YEAST AND MICROORGANISMS TRANSFORMED THEREWITH

[75] Inventors: Shing Chang, Hercules; James H. Meade, Pinole, both of Calif.

[73] Assignee: Cetus Corporation, Emeryville, Calif.

[21] Appl. No.: 346,258

[22] Filed: Feb. 5, 1982

Related U.S. Application Data

[63] Continuation-in-part of Ser. No. 232,435, Feb. 9, 1981, abandoned.

[51] Int. Cl.³ .................... C12N 1/20; C12N 15/00; C12N 1/18; C12N 1/00
[52] U.S. Cl. .................. 435/253; 435/172.3; 435/256; 435/317; 935/28; 935/29; 935/69; 935/73
[58] Field of Search ............... 435/172, 317, 253, 256

[56] References Cited

U.S. PATENT DOCUMENTS

4,387,162 6/1983 Aigle et al. .................. 435/172

OTHER PUBLICATIONS

Hollenberg, Plasmids of Medical Environmental and Commercial Importance, pp. 481–492 (1979).
Bolivar et al., Methods in Enzymology, vol. 68, pp. 245–267 (1979).
Hsiao et al., PNAS (U.S.) 76, pp. 3829–3833 (1979).
Broach et al., Gene 8, pp. 121–133 1979.
Gerband et al., Gene 5, pp. 233–253 (1979).
Beggs, Nature 275, pp. 104–109 (1978).
Hinnen et al., PNAS (U.S.) 75, pp. 1929–1933 (1978).
Betlach et al., Fed. Proc. 35 pp. 2037–2043 (1976).
Chang, Annie & Cohen, Stanley "Construction and Characterization of Amplifiable Mulicopy DNA Cloning Vehicles Derived from the P15A Cryptic Miniplasmid" *Journal of Bacteriology* 134: 1141–1156 (1978).
Cohen, J., Eccleshall, T., Needleman, R., Federoff, H., Buchferer, B., & Marmur, J. "Functional Expression in Yeast of the *Escherichia coli* Plasmid Gene Coding for Chloramphenicol Acetyltransferase" *Proc. Natl. Acad. Sci.* 77: 1078–1082 (1980).
Jimenez, A. & Davies, J. "Expression of Transposable Antibiotic Resistance Element in Saccharomyces" 287: 869–871 (1980) *Nature*.
Stinchcomb, D., Struhl, K., & Davis, R. "Isolation and Characterization of a Yeast Chromosomal Replicator" *Nature* 282: 39–43 (1979).
Struhl, K., Stinchcomb, D., Scherer, S., & Davis R. "High-Frequency Transformation of Yeast: Autonomous Replication of Hybrid DNA Molecules" *Proc. Natl. Acad. Sci.* 76: 1035–1039 (1979).
Tschumper, G. & Carbon, J. "Sequence of a Yeast DNA Fragment Containing a Chromosomal Replicator and the TRPI Gene" *Gene* 10: 157–166 (1980).

*Primary Examiner*—Alvin E. Tanenholtz
*Attorney, Agent, or Firm*—Albert P. Halluin; Virginia H. Meyer; William J. Scanlon

[57] ABSTRACT

Chimeric plasmids capable of transforming bacteria and yeast are described. The plasmids carry the Cm (chloramphenicol resistance) gene and the Tc (tetracycline resistance) gene as selectable markers. The Cm gene allows the plasmids to be selected for in wild-type strains of the yeast *Saccharomyces cerevisiae*. The Tc gene allows heterologous genes cloned into the plasmids to be selected for in *Escherichia coli* bacteria.

6 Claims, 7 Drawing Figures

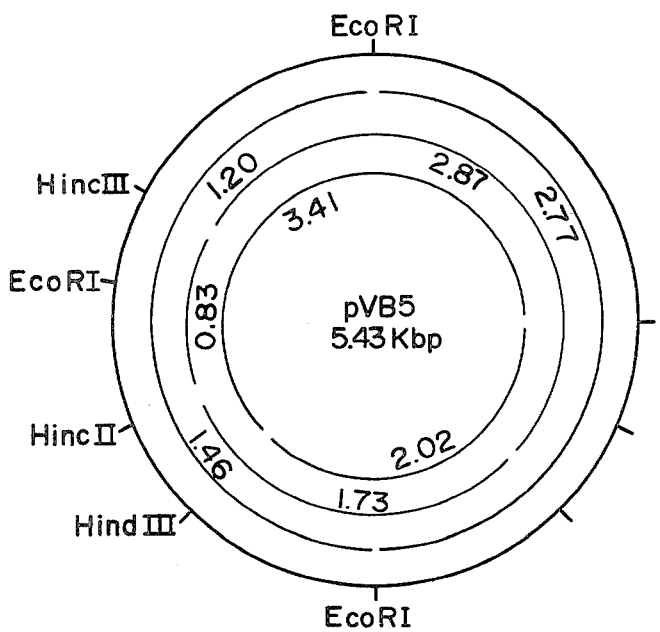
FIG. 4
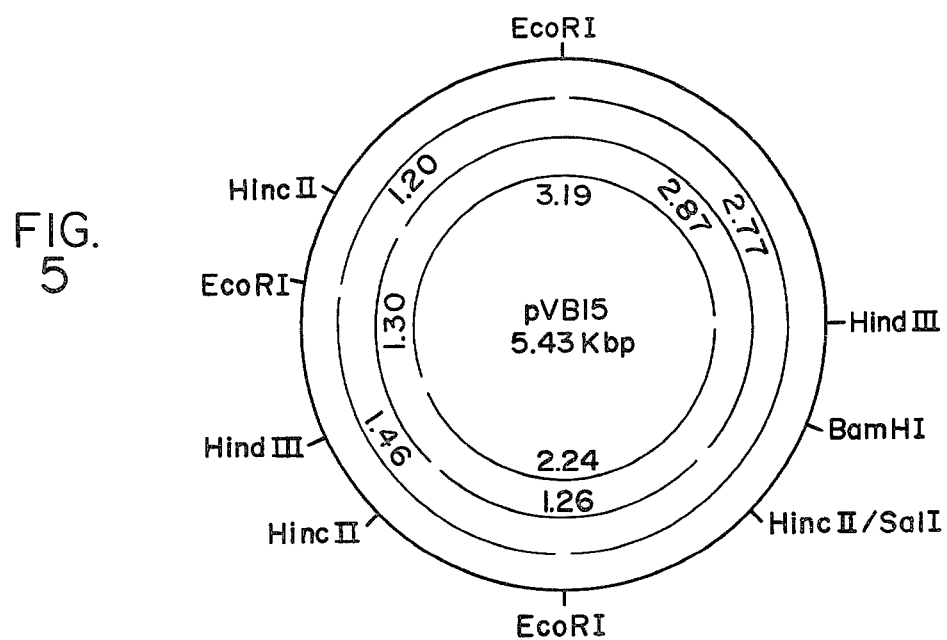
FIG. 5
FIG. 6
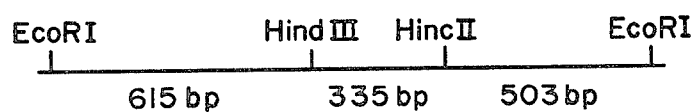

FIG. 7

DIAGRAM OF AGAROSE GEL OF RESTRICTION ENZYME DIGESTS OF pACYC184, pVB15, pVB5 AND pLC544

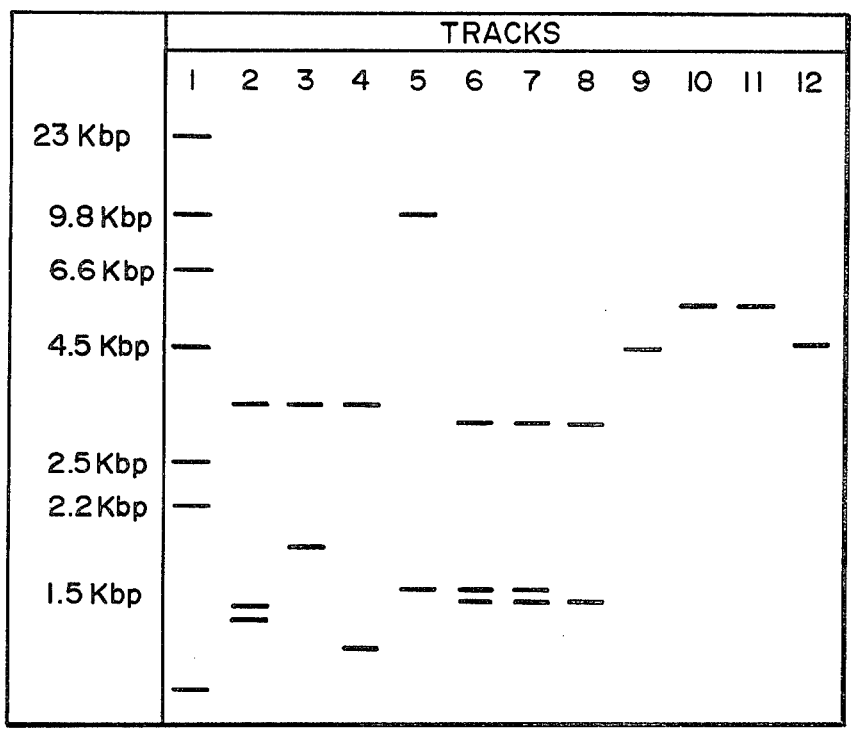

TRACK
1. ____ DNA MOLECULAR WEIGHT STANDARDS
2. ____ pVB15 DIGESTED WITH HincII
3. ____ pVB5 DIGESTED WITH HincII
4. ____ pACYC184 DIGESTED WITH HincII
5. ____ pLC544 DIGESTED WITH EcoRI
6. ____ pVB15 DIGESTED WITH EcoRI
7. ____ pVB5 DIGESTED WITH EcoRI
8. ____ pACYC184 DIGESTED WITH EcoRI AND AvaI
9. ____ pACYC184 DIGESTED WITH EcoRI
10. ____ pVB15 DIGESTED WITH BamHI
11. ____ pVB5 DIGESTED WITH BamHI
12. ____ pACYC184 DIGESTED WITH BamHI ns of Application Ser. No. 232,435 filed Feb. 9, 1981, now abandoned. This invention relates to molecular biology and, more particularly, to the so-called art of recombinant DNA. Specifically, the invention relates to the construction of improved chimeric plasmids that replicate in bacteria and yeast. These chimeric plasmids carry genetic markers which make them especially suitable for industrial yeast production of cloned gene products.

CHIMERIC PLASMIDS THAT REPLICATE IN BACTERIA AND YEAST AND MICROORGANISMS TRANSFORMED THEREWITH

This application is a continuation-in-part of application Ser. No. 232,435 filed Feb. 9, 1981, now abandoned. This invention relates to molecular biology and, more particularly, to the so-called art of recombinant DNA. Specifically, the invention relates to the construction of improved chimeric plasmids that replicate in bacteria and yeast. These chimeric plasmids carry genetic markers which make them especially suitable for industrial yeast production of cloned gene products.

The invention discloses two unique genetically engineered plasmids: plasmid pVB5 and plasmid pVB15. *E. coli* strains containing these two plasmids have been deposited with the American Type Culture Collection, Rockville, Md., 20852. The *E. coli* strain containing plasmid pVB5 has been assigned ATCC number 31804; the *E. coli* strain containing plasmid pVB15 has been assigned ATCC number 31803. Applicants have directed that the strains containing the plasmids be freely available to the general public upon the issuance of a U.S. patent.

As is well known, recent advances in the rapidly developing field of recombinant DNA technology make it possible to construct chimeric plasmids which allow a variety of cloned genes to be expressed in microorganisms. Some of these plasmids replicate in more than one type of microorganisms, e.g., in both bacteria and yeast. K. Struhl et al, PNAS, 76:1035–1039 (1979).

However, the plasmids disclosed thus far are not suitable for a large scale industrial yeast production of cloned gene products because of the types of genetic markers used to select for the presence of the plasmids in bacteria and yeast. For example, some of the plasmids (vectors) disclosed by Struhl et al, supra, use of the his3, trp1 and ura3 genes as selectable markers. Use of these genes as markers means that the plasmids are only detectable in auxotrophic strains of yeast. As a result, commercially available wild-type strains of yeast will have to be mutated to his3−, trp1− and ura3− strains before the transformed microorganisms are detectable. Such a mutational requirement severely limits the industrial usefulness of these plasmids. Therefore it is an object of the present invention to create chimeric plasmids carrying selectable gene markers detectable in commercially available wild-type strains of yeast.

Another plasmid disclosed by Struhl et al, supra, uses resistance to the antibiotic tetracycline as a selectable marker. The gene coding for the protein that confers tetracycline resistance is only expressed in bacteria; thus use of this marker does not allow the plasmid to be selected for in yeast. As a result, the industrial usefulness of this plasmid is also severely limited. Therefore, it is an object of the present invention to create an industrially useful chimeric plasmid carrying a genetic marker which allows the plasmid to be selected for in yeast.

J. Cohen et al, PNAS 77:1078–1082 (1980) disclosed the construction of a chimeric plasmid carrying the *E. coli* R factor-derived chloramphenicol resistance gene. Although these investigators are able to demonstrate expression of this gene in the yeast *S. cerevisiae*, their vector does not carry a second marker gene which easily allows genes cloned into the plasmid to be selected for in bacteria. Lack of such a second marker limits the industrial usefulness of such a plasmid. Therefore it is an object of the present invention to create a chimeric plasmid carrying a marker gene which easily allows genes cloned into the plasmid to be selected for in bacteria.

A. Jimenez and J. Davies, Nature 287:869–871 (1980) disclose use of antibiotic G418 as a selective agent. Although these authors allude to the advantages of such a system, Jimenez and Davies do not use a plasmid containing a second gene marker, coding for a protein conferring resistance to a second antibiotic, to allow genes cloned into the plasmid to be selected for in bacteria. As with the plasmid used by Cohen et al, lack of such a second marker also limits the industrial usefulness of the Jimenez and Davies plasmid as a cloning vector. Also, at the present time antibiotic G418 is not a commercially available product. Having the selectivity of the plasmid depend upon a product that is not commercially available also severely limits the industrial usefulness of such a vector. Therefore, it is an object of the present invention to create chimeric plasmids carrying marker genes conferring resistance to antibiotics that are currently commercially available.

Other objects of the invention will become apparent to those skilled in the art from the following description, taken in connection with the accompanying drawings wherein:

FIG. 4 is a diagram of chimeric plasmid pVB5 which indicates the nucleotide kilobase pairs that result when the plasmid is digested with various restriction endonucleases;

FIG. 5 is a diagram of chimeric plasmid pVB15 which indicates the nucleotide kilobase pairs that result when the plasmid is digested with various restriction endonucleases;

FIG. 6 is a diagram of the yeast ars1 DNA fragment which indicates the nucleotide kilobase pairs that result when the plasmid is digested with various restriction endonucleases; and FIG. 7 is a diagram of an agarose gel of restriction enzyme digests of plasmids pACYC184; pVB5, pVB15 and pLC544.

Figure 1:
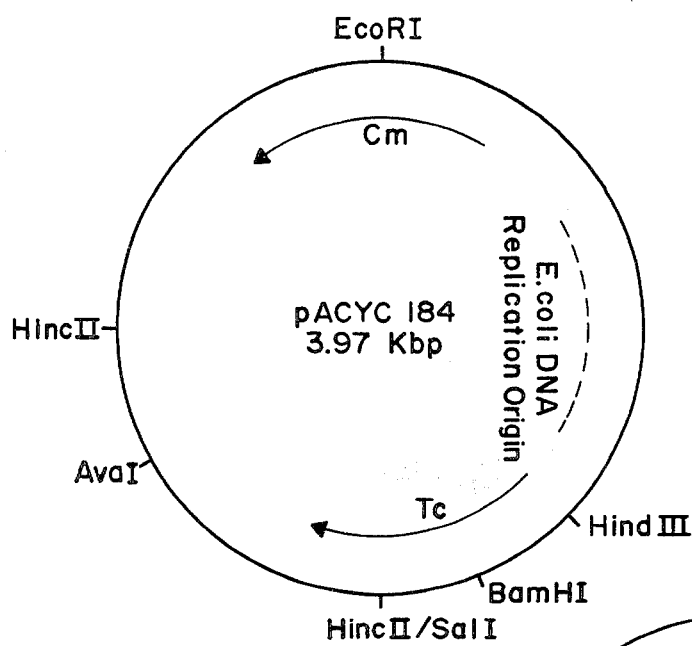
FIG. 1 is a diagram of *E. coli* plasmid pACYC184 which indicates the approximate locations of the Cm and Tc genes.

Very generally the invention involves construction of chimeric plasmids which can replicate in yeast and bacteria. Such plasmids carry one genetic marker that allows genes cloned in the plasmids to be selected for in bacteria, and another that allows the plasmids themselves to be selected for yeast. The genetic markers are genes coding for proteins that confer resistance to common commercially available antibiotics. Thus the plasmids are especially suitable for industrial production of cloned gene products in yeast because they do not require the use of auxotrophic strains.

The plasmids are constructed by combining an *E. coli* plasmid and a fragment of *S. cerevisiae* yeast DNA. The *E. coli* plasmid carries all of the genes necessary for replication of the plasmid in *E. coli*. It also carries the Tc gene (coding for a protein that confers resistance to tetracycline) and the Cm gene (coding for a protein that confers resistance to chloramphenicol). The Tc gene is used as a marker to allow genes cloned into the plasmids to be selected for in bacteria. The Cm gene is used as a marker to allow the plasmids to be selected for in wild-type strains of *S. cerevisiae*. The fragment of *S. cerevisiae* yeast DNA contains all of the genes necessary for replication of the plasmid in this strain of yeast. The plasmids thus formed, and disclosed herein, have been designated plasmid pVB5 (ATCC No. 31804) and plasmid pVB15 (ATCC No. 31803). The two plasmids differ from one another only in the orientation of the yeast DNA fragment in the *E. coli* plasmid. Both plasmid pVB5 and pVB15 transform *E. coli* bacteria and the *S. cerevisiae* yeast.

In the most preferred form of the present invention both plasmids are constructed by combining a segment of yeast DNA, ars1, characterized by K. Stinchcomb et al, Nature 282:39–43 (1979), with *E. coli* plasmid pACYC184, characterized by A. Chang and S. Cohen, J. Bacteriol. 134:1141–1156 (1978). In the disclosed embodiment, plasmids pVB5 and pVB15 are constructed by ligating the ars1 yeast DNA fragment with *E. coli* plasmid pACYC184. The bacterial DNA and the yeast DNA could be combined by other means known to the art, such as insertion of the fragments into a third vector.

*E. coli* plasmid pACYC184 contains all of the genes necessary for replication in *E. coli*. It also contains the gene Cm, which codes for the protein that confers resistance to the common antibiotic chloramphenicol, and the gene Tc, which codes for the protein that confers resistance to the common antibiotic tetracycline. The gene Cm can be functionally expressed in both *E. coli* and yeast; thus it provides an excellent genetic marker for selecting for the presence of the plasmids in both organisms. The gene Tc is important because it provides an excellent means of screening for the insertion of additional DNA sequences (cloned genes) into the plasmids. The gene Tc is functionally expressed in *E. coli*. Both chloramphenicol and tetracycline are available commercially in the amounts necessary for large scale industrial utilization of plasmids carrying these resistance markers.

PLASMID CONSTRUCTION

*E. coli* plasmid pACYC184 DNA was prepared for use by digesting 2.6 μg of pACYC184 DNA with four units of AvaI endonuclease in AL buffer to a final volume of 339 μl, for 1 hour at 37° C. The components of AL buffer are listed infra. The digestion mixture was heated at 65° C. for 5 minutes to inactivate the endonuclease. The DNA was precipitated from the solution with cold 100% ethanol and then dried by lyophilization.

The action of enconuclease AvaI results in single stranded, so-called "sticky" ends being left on the cut ends of the digested pACYC184 plasmid. These "sticky" ends were converted to so-called "blunt" ends by complementary base addition catalyzed by the large fragment of *E. coli* DNA polymerase I. This conversion was accomplished by resuspending the lyophilized DNA in 10 μl of modified ligation buffer (described infra) and then heating the DNA to 70° C. for 2 minutes in order to open the "sticky" ends. The mixture was cooled to 0° C. on ice and 1 μl of DNA polymerase I—large fragment (0.7 units per μl) was added. After 5 minutes, the mixture was heated at 70° C. for an additional 5 minutes to inactivate the polymerase. The mixture was then frozen at −20° C. for later use. *E. coli* plasmid pACYC184 is diagramed in FIG. 1.

Figure 2:
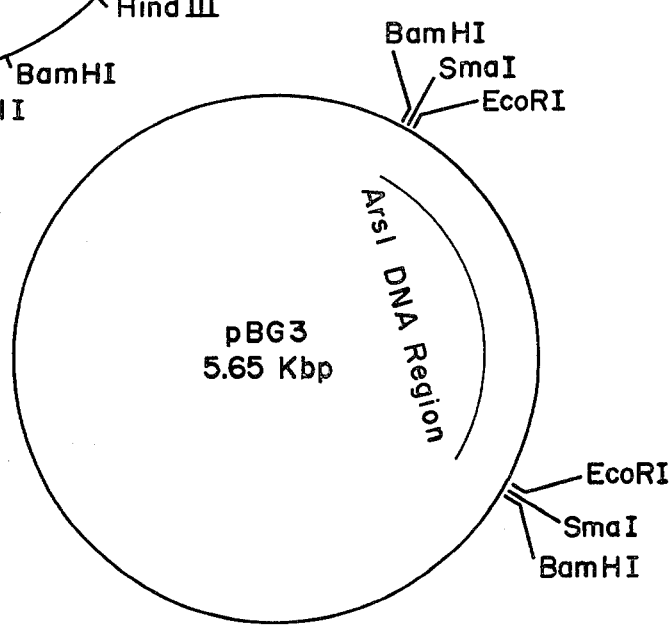
FIG. 2 is a diagram of chimeric plasmid pVB3 which indicates some of the restriction endonucleases that can be used to remove the yeast ars1 DNA fragment.

In order to eliminate the single stranded ends of the yeast ars1 DNA fragment, it was incorporated into a plasmid known as pBG3. This plasmid is diagramed in FIG. 2. The ars1 fragment was then removed from plasmid pBG3 by digesting 14 μg of plasmid pBG3 with 20 units of SmaI endonuclease. Digestion was carried out in R buffer plus 6 mM KCl, to a final volume of 800 μl, for 1 hour at 37° C. The DNA fragments were then separated by electrophoresis on a 0.8% agarose gel (4 tracks at 200 μl per track). The bands of DNA corresponding to the ars1 fragment were eluted from the gel and precipitated with ethanol using standard procedures. Since the pBG3 plasmid was digested with SmaI, an endonuclease which produces "blunt" ends rather than "sticky" ends, no further modification of the ars1 fragment was necessary.

Plasmid pACYC184 was then ligated with the ars1 DNA fragment by mixing 2.5 μg of pACYC184 DNA with 4.8 μg of the ars1 fragment, in the presence of 1 μl of 10 mM ATP and T4 ligase in ligation buffer to a final volume of 11 μl. The DNA ligation reaction mixture was incubated at 16° C. for 21 hours and then the 11 μl was diluted with 14 μl of TE buffer for use in transformation of *E. coli* strain JA300. Ligation buffer and TE buffer are described infra.

TRANSFORMATION OF JA300

Transformation of *E. coli* strain JA300 was carried out according to standard procedures except that, prior to plating, the cells were centrifuged and resuspended in 0.4 μl of VB medium. Cells from the transformation mix were plated on VB medium, VB medium plus chloramphenicol (20 μg per μl) and on No. 454 medium, a complex complete growth medium. Nontransformed JA300 cells were also plated on VB medium. VB medium and No. 454 medium are described infra. It should be noted that VB medium contains casamino acids which lack the amino acid tryptophan.

JA300 is a tryptophan-requiring, chloramphenicol-sensitive strain of *E. coli*. The ars1 DNA fragment contains the yeast trp1 gene; this gene can be expressed in *E. coli* and can make the JA300 strain tryptophan non-requiring (trp+). Therefore, a simple determination of the frequency of desired transformants can be made by comparing the difference in the number of tryptophan non-requiring colonies between untreated and DNA-treated JA300 cells. In one experiment, DNA treatment resulted in an 8-fold increase in trp+ cells: 1.6 trp+/$10^8$ cells in the untreated cell sample versus 13.4 trp$^{30}$/$10^8$ cells in the DNA-treated sample.

CHARACTERIZATION OF PLASMID DNA IN THE *E. COLI* TRANSFORMANTS

Approximately 90% of the trp+ *E. coli* cells were probably transformants containing the desired plasmid. 82 colonies from the transformation plates (VB medium and VB medium plus chloramphenicol) were picked and retested for the tryptophan requirement and the chloramphenicol resistance. Of the 82 colonies picked, 72 were trp+ and chloramphenicol-resistant. 25 of these picked strains were checked for plasmids using a quick plasmid screen procedure and then compared to two purified plasmid DNAs, i.e. plasmid pACYC184 (4.0 kilobase pairs) and plasmid pHD5101 (5.1 kilobase pairs). One Kbp is 1,000 nucleotide base pairs. *E. coli* plasmid pACYC184 plus the yeast ars1 fragment would result in a plasmid containing about 5.45 Kbp. 21 of the 25 strains examined contain plasmids equal or greater in size than the 5.45 Kbp expected; the larger plasmids are most likely multimers. 6 of these plasmids were examined in more detail by restriction endonuclease digestion followed by agarose gel electrophoresis. Two plasmids, designated as plasmid pVB5 and plasmid pVB15, appear to result from ligation of the ars1 yeast fragment with *E. coli* plasmid pACYC184. The plasmids are identical except for the orientation of the yeast ars1 fragment in the *E. coli* DNA.

Figure 3:
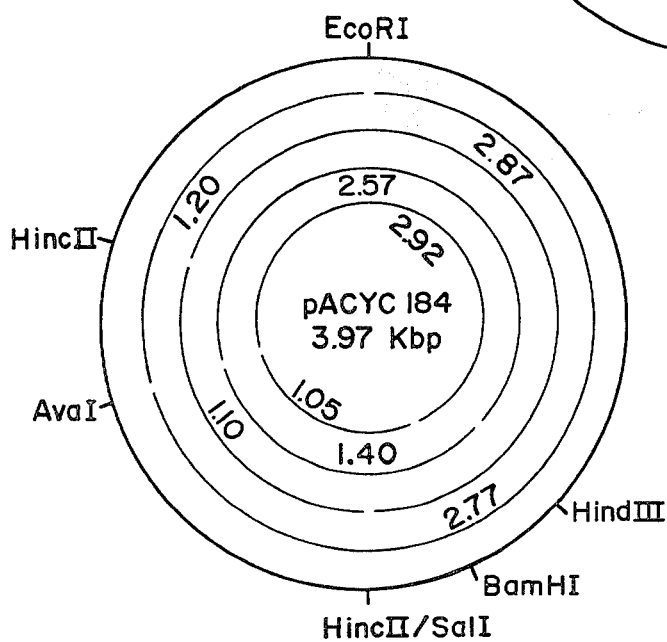
FIG. 3 is a diagram of *E. coli* plasmid pACYC184 which indicates the nucleotide kilobase pairs that result when the plasmid is digested with various restriction endonucleases.

FIG. 3 is a diagram of *E. coli* plasmid pACYC184 showing the position of some of the restriction endonuclease digestion sites, and the DNA segments generated by digestion with these restriction endonucleases when used either alone or in combination. Chimeric plasmids pVB5 and pVB15 are diagramed in FIGS. 4 and 5 respectively. The map for *E. coli* plasmid pACYC184 is the same as that published previously by Chang and Cohen, supra, except for the addition of the AvaI restriction site. A map for the ars1 segment of the yeast DNA has been published by G. Tschumper and J. Carbon, Gene 10:157–166 (1980) and is diagramed with a few of the restriction endonuclease sites in FIG. 6. The maps of plasmid pVB5 and pVB15 differ in the orientation of the ars1 fragment in the AvaI site of plasmid pACYC184. The assignment of plasmid pVB5 and plasmid pVB15 to their appropriate maps was determined by agarose gel analysis of the restriction endonuclease digests.

A set of restriction endonuclease digests of plasmids pACYC184, pVB5, pVB15, and pLC544 separated on agarose gel is diagramed in FIG. 7. Tracks 10, 11 and 12 are digests of three of the plasmids with the endonuclease BamHI. Since BamHI cuts each plasmid only once, it was determined that the size of pVB5 and pVB15 are between 4.5 and 6.6 Kbp, based on the molecular weight standards in track number 1.

Digestion of *E. coli* plasmid pACYC184 with the endonuclease EcoRI (track number 9) again produces a single full length fragment; however digestion with both EcoRI and AvaI (track number 8) produces two fragments of approximately 2.77 and 1.20 Kbp. Digestion of pVB5 (track number 7) and pVB15 (track number 6) with EcoRI produces three bands; two of the bands correspond to the bands in the EcoRI-AvaI digest of pACYC184 (track number 8) and the third corresponds to the 1.45 Kbp band in track 5 which is known to be the ars1 fragment. Thus the data is compatible with the genetic maps shown in FIGS. 4 and 5. The insertion site of the ars1 fragment into pACYC184 was confirmed by digestion with the restriction endonuclease HincII. HincII cut pACYC184 in two places, resulting in fragments of 2.87 and 1.10 Kbp. Digestion of pVB5 and pVB15 with HincII produced three fragments, one of 2.87 Kbp and two smaller pieces. Since the third HincII site is known to be in the ars1 DNA segment, the size of the two small fragments allowed the orientation of the ars1 fragment in the plasmid to be determined.

TRANSFORMATION OF YEAST WITH PLASMIDS pVB5 AND pVB15

After the pVB series of plasmids had been constructed and characterized with the quick plasmid screen and restriction enzyme digests, plasmids pVB5 and pVB15 were chosen for use in the transformation experiments because they contained the ars1-trp1 DNA inserted in opposite directions in plasmid pACYC184.

Yeast strain C483 was chosen for transformation. Strain C483 is a haploid *S. cerevisiae* of mating type a that is defective in a gene for tryptophan biosynthesis (trp1) and cannot ferment galactose (gal2) or maltose (mal). Since yeast strain C483 cannot grow without tryptophan being added to the medium transformation frequencies with plasmids pVB5 and pVB15 were measured by monitoring growth of DNA-treated cells on media without tryptophan. For purposes of this disclosure minimal media without tryptophan is called selective media and minimal media with added tryptophan is called complete media.

The transformation experiments involved three steps: protoplasting the yeast, i.e. removing the yeast cell walls; exposing them to DNA; and treating them with an agent that causes the uptake of the plasmid DNA. The source of the DNA was either plasmid pVB5 or pVB15. Approximately $2.3 \times 10^8$ protoplasts from strain C483 were incubated with 10 µg of plasmid DNA from pVB5 or pVB15 for 15 minutes at room temperature. In order to encourage the uptake of the plasmid DNA, polyethylene glycol (PEG) was added and the mixture incubated for an additional 40 minutes. The polyethylene glycol is a 44% solution in 10 mM tris-HCl plus 10 mM $CaCl_2$ at pH 7.5. Dilution and plating on either selective or complete media followed directly after the 40 minute incubation in PEG.

Protoplasts that were transformed with plasmid pVB5 or pVB15 were plated on selective medium, as were protoplasts that had been through the same series of treatments but had never been exposed to plasmid DNA. These untransformed protoplasts were controls that showed the frequency with which strain C483 reverted from requiring tryptophan to being able to make its own. For purposes of this disclosure the C483 cells now able to synthesize tryptophan are referred to as back-mutants.

Transformation with plasmids pVB5 and pVB15 led to titers of $6.3 \times 10^4$ and $5.48 \times 10^4$ transformants per $2.3 \times 10^8$ protoplasts respectively; the back-mutant titer was $1.1 \times 10^3$ reverting per $2.3 \times 10^8$ protoplasts. In other words, transformation with plasmids pVB5 or pVB15 led to a 50–60 fold increase in the occurrence of colonies on plates without tryptophan. Expressed in a slightly different way, plasmid pVB5 yielded $6.19 \times 10^3$ colonies per µg of DNA added and plasmid pVB15 yielded $5.37 \times 10^3$ colonies/µg DNA added.

Both plasmids pVB5 and pVB15 contain the yeast ars1 DNA fragment. Plasmids containing this fragment are expected to transform yeast at a frequency of $5-50 \times 10^3$ colonies per µg of DNA (D. Stinchcomb et al, PNAS 77:4559–4563 (1980). The results of this disclosure concur with the Stinchcomb et al expectation. The frequencies of transformation for plasmid pVB5 and pVB15 are not drastically different; thus it appears that the orientation of the ars1-trp1 DNA fragment in the pVB plasmids does not significantly influence transformation.

Complete medium was used for plating further controls for this experiment. The complete medium demonstrated the protoplasts' ability to regenerate cell walls and form colonies. These complete medium controls indicated that the protoplasts are healthy and that approximately 5.8% of those present in the original mix were capable of forming colonies on minimal media. This percentage is called the regeneration efficiency;

the normal regeneration efficiency range for yeast strain C483 is between 5 and 20%. Thus this experiment demonstrates that plasmids pVB5 and pVB15 transformed yeast strain C483 at frequencies consistent with those expected for plasmids carrying an ars1 fragment, and that orientation of insertion of the ars1-trp1 DNA does not appear to significantly influence transformation frequencies.

To show that the chloramphenicol resistance gene could be used as a selectable marker in yeast, we plated cells of strain C483 and cells of strain C483 transformed with pVB5 on chloramphenicol gradient plates. The gradient plates were prepared in 90 mm square petri dishes (nominally 100 mm). A 25 ml portion of minimal media containing tryptophan was mixed with 0.5 ml of DMSO containing 0.7 mg of chloramphenicol and was allowed to solidify in the petri dishes on a slanted table. An additional 25 ml of minimal media containing tryptophan was added while the plates were horizontal. The gradient plates were allowed to equilibrate overnight. After spotting both strains on the gradient plates, we incubated the plates at 30C. The plates were checked after 2 and 5 days of incubation, and at both times, the strain transformed with pVB5 grew at significantly higher concentrations of chloramphenicol than did the untransformed strain. This difference is satisfactory for selection of transformants on the basis of resistance to chloramphenicol.

It may be seen, therefore, that the invention discloses chimeric plasmids capable of transforming $E. coli$ bacteria and $S. cerevisiae$ yeast. The plasmids are especially suitable for industrial production of cloned gene products in yeast because they can be used with wild-type strains of $S. cerevisiae$. The plasmids carry the Cm and Tc genes as selectable markers. The Cm gene allows the plasmids to be selected for in $S. cerevisiae;$ the Tc gene allows heterologous genes cloned into the plasmids to be selected for in $E. coli$.

Various modifications of the invention in addition to those shown and described herein will become apparent to those skilled in the art from the foregoing description and accompanying drawings. Such modifications are intended to fall within the scope of the appended claims.

MEDIA AND BUFFERS

AL Buffer (10× Concentration)

100 mM Tris-HCl, pH 7.9
79 mM MgCl$_2$
600 mM NaCl
60 mM β-mercaptoethanol

Prepare as follows:
17 ml DDI water
10 ml 1M Tris-HCl pH 7.9
7 ml 1M MgCl$_2$
60 ml 1M NaCl
Autoclave for 20 minutes.
After autoclaving add 6.0 ml of 1M β-mercaptoethanol

Ligation Buffer (10× Concentration)

500 mM tris-HCl, pH 7.4
10 mM EDTA, pH 8.1
100 mM MgCl$_2$
100 mM dithiothreitol

Modified Ligation Buffer

10 μl 10× Ligation buffer
10 μl 100 μM dATP
10 μl 100 μM dGTP
10 μl 100 μM dCTP
10 μl 100 μM dTTP
50 μl glass distilled H$_2$O
1 μl 1% bovine serum albumin

R Buffer (10× Concentration)

100 mM Tris-HCl, pH 7.8
70 mM MgCl$_2$
60 mM β-mercaptoethanol
1 mg/ml gelatin

Prepare as follows:
20 ml DDI water
10 ml 1M Tris-HCl pH 7.8
7 ml 1M MgCl$_2$
0.1 g gelatin (heat to dissolve gelatin)
Add DDI water to 94 ml.
Autoclave 20 minutes.
After autoclaving add 6.0 ml of 1M β-mercaptoethanol

TE Buffer (10× Concentration)

100 mM Tris-HCl, pH 8.0
1 mM EDTA

VB Medium 0.2 g MgSO$_4$.7H$_2$O
2.0 g Citric Acid.H$_2$O
10.0 g K$_2$HPO$_4$
3.5 g Na(NH$_4$)HPO$_4$.4H$_2$O
844 ml distilled water after autoclaving add:

25 ml sterile 40% glucose
100 ml sterile 2% casamino acids
1 ml sterile 1% vitamin B1
10 ml sterile 0.1% thymidine
20 ml sterile 0.1% chloramphenicol

#454 Medium

Difco Antibiotic Medium #2: 25.5 gms
  Composition:
  Bacto Beef Extract: 1.5 gm
  Bacto Yeast Extract: 3 gm
  Bacto Peptone: 6 gm
  Bacto Agar: 15 gm
Water: 1000 ml
Autoclave.

Citations

A. Chang and S. Cohen, J. Bacteriol. 134:1141–1156 (1978).
J. Cohen et al, PNAS 77:1078–1082 (1980).
A. Jimenez and J. Davies, Nature 287:869–871 (1980).
K. Stinchcomb et al, Nature 282:39–43 (1979).
K. Struhl et al, PNAS 76:1035–1039 (1979).
G. Tschumper and J. Carbon, Gene 10:157–166 (1980).

What is claimed is:
1. Chimeric plasmid pVB5.
2. Chimeric plasmid pVB15.

3. *Escherichia coli* cells transformed with plasmids selected from the group consisting of pVB5 and pVB15.

4. Cells according to claim 3 transformed with plasmid pVB5 and deposited in the American Type Culture Collection as deposit no. 31804.

5. Cells according to claim 3 transformed with plasmid pVB15 and deposited in the American Type Culture Collection as deposit no. 31803.

6. *Saccharomyces cerevisiae* cells transformed with plasmids selected from the group consisting of pVB5 and pVB15.

* * * * *